(12) United States Patent
Clear et al.

(10) Patent No.: US 10,894,978 B2
(45) Date of Patent: Jan. 19, 2021

(54) GENETIC TEST FOR DETECTING CONGENITAL ADRENAL HYPERPLASIA

(71) Applicant: Bioo Scientific Corporation, Austin, TX (US)

(72) Inventors: Colby Clear, Austin, TX (US); Radmila Hrdlickova, Austin, TX (US); Jiri Nehyba, Austin, TX (US); Dylan Fox, Austin, TX (US)

(73) Assignee: BIOO SCIENTIFIC CORPORATION, Austin, TX (US)

( * ) Notice: Subject to any disclaimer, the term of this patent is extended or adjusted under 35 U.S.C. 154(b) by 310 days.

(21) Appl. No.: 15/847,816

(22) Filed: Dec. 19, 2017

(65) Prior Publication Data

US 2019/0185925 A1    Jun. 20, 2019

(51) Int. Cl.
*C12Q 1/68* (2018.01)
*C12Q 1/6855* (2018.01)
*C12Q 1/6827* (2018.01)
*C12Q 1/6883* (2018.01)

(52) U.S. Cl.
CPC ......... *C12Q 1/6855* (2013.01); *C12Q 1/6827* (2013.01); *C12Q 1/6883* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| 2004/0209259 | A1* | 10/2004 | Keen-Kim | ........... | C12Q 1/6883 435/6.1 |
| 2006/0029930 | A1* | 2/2006 | Keen-Kim | ........... | C12Q 1/6883 435/5 |
| 2016/0188793 | A1 | 6/2016 | Muzzey et al. | | |

OTHER PUBLICATIONS

Hamady M, Walker JJ, Harris JK, Gold NJ, Knight R. Error-correcting barcoded primers for pyrosequencing hundreds of samples in multiplex. Nat Methods. Mar. 2008; 5(3):235-7. Epub Feb. 10, 2008. (Year: 2008).*
Canturk C, Baade U, Salazar R, Storm N, Pörtner R, Höppner W. Sequence analysis of CYP21A1P in a German population to aid in the molecular biological diagnosis of congenital adrenal hyperplasia. Clin Chem. Mar. 2011; 57(3):511-7. Epub Dec. 9, 2010. (Year: 2011).*
Canturk C. Development of a mass spectrometry-based test panel for the molecular genetic analysis of CYP21A2 and its pseudogene for the diagnostics of CAH (2013, Doctoral dissertation, Universitatsbibliothek der Technischen Universitat Hamburg-Harburg). (Year: 2013).*
Chan et al. Molecular analysis of congenital adrenal hyperplasia due to 21-hydroxylase deficiency in Hong Kong Chinese patients. Steroids. Sep.-Oct. 2011; 76(10-11):1057-62. Epub Apr. 28, 2011. (Year: 2011).*
Greene CN, Cordovado SK, Turner DP, Keong LM, Shulman D, Mueller PW. Novel method to characterize CYP21A2 in Florida patients with congenital adrenal hyperplasia and commercially available cell lines. Mol Genet Metab Rep. Aug. 8, 2014; 1:312-323. (Year: 2014).*
Knapp M, Stiller M, Meyer M. Generating barcoded libraries for multiplex high-throughput sequencing. Methods Mol Biol. 2012; 840: 155-70. (Year: 2012).*
Lee HH, Lee YJ, Lin CY. PCR-based detection of the CYP21 deletion and TNXA/TNXB hybrid in the RCCX module. Genomics. May 2004; 83(5):944-50. (Year: 2004).*
Lee HH. Variants of the CYP21A2 and CYP21A1P genes in congenital adrenal hyperplasia. Clin Chinn Acta. Mar. 15, 2013; 418:37-44. Epub Jan. 9, 2013. Review. (Year: 2013).*
Lee HH. Mutational analysis of CYP21A2 gene and CYP21A1P pseudogene: long-range PCR on genomic DNA. Methods Mol Biol. 2014; 1167:275-87 (Year: 2014).*
Ma et al. Molecular analysis of the CYP21A2 gene in Chinese patients with steroid 21-hydroxylase deficiency. Clin Biochem. Apr. 2014; 47(6):455-63. Epub Feb. 3, 2014. (Year: 2014).*
Meyer M, Kircher M. Illumina sequencing library preparation for highly multiplexed target capture and sequencing. Cold Spring Harb Protoc. Jun. 2010; 2010(6): 155-170. (Year: 2010).*
Quail MA, Swerdlow H, Turner DJ. Improved protocols for the illumina genome analyzer sequencing system. Curr Protoc Hum Genet. Jul. 2009;Chapter 18:Unit 18.2. pp. 18.2.1-18.2.27. (Year: 2009).*
Vrzalova et al. Chimeric CYP21A1P/CYP21A2 genes identified in Czech patients with congenital adrenal hyperplasia. Eur J Med Genet. Mar.-Apr. 2011; 54(2):112-7. Epub Oct. 21, 2010. (Year: 2011).*
Xu Z, Chen W, Merke DP, McDonnell NB. Comprehensive mutation analysis of the CYP21A2 gene: an efficient multistep approach to the molecular diagnosis of congenital adrenal hyperplasia. J Mol Diagn. Nov. 2013; 15(6):745-53. Epub Sep. 23, 2013. (Year: 2013).*

(Continued)

*Primary Examiner* — Teresa E Strzelecka
*Assistant Examiner* — Olayinka A Oyeyemi
(74) *Attorney, Agent, or Firm* — James S. Keddie; Bozicevic, Field & Francis LLP (57) ABSTRACT

A method for amplifying a CYP21A2 gene and/or a CYP21A2 gene chimera from a sample is provided. In some embodiments, the method may comprise amplifying a product from a sample comprising human genomic DNA by PCR using a forward primer that is complementary to a sequence that is duplicated in a bimodular human RCCX locus and a reverse primer that is complementary to a sequence that occurs only once in the bimodular human RCCX locus at a position that is downstream of the CYP21A2 gene. Methods for analyzing the amplification product are also provided.

11 Claims, 4 Drawing Sheets
Specification includes a Sequence Listing.

(56) References Cited

OTHER PUBLICATIONS

Larsen et al. Improved detection of rare HIV-1 variants using 454 pyrosequencing. PLoS One. 2013; 8 (10):e76502. Published Oct. 2, 2013. (Year: 2013).*
Banlaki et al., "Intraspecific Evolution of Human RCCX Copy Number Variation Traced by Haplotypes of the CYP21A2 Gene", Genome Biol. Evol., 2012, 5(1):98-112.
Cradic et al., "A simple method for gene phasing using mate pair sequencing", BMC Medical Genetics, 2014, 15:19, 8 pages.
Haider et al., "Structure—phenotype correlations of human CYP21A2 mutations in congenital adrenal hyperplasia", PNAS, 2013, 110(7): 2605-2610.
Hannah-Shmouni et al., "Genetics of Congenital Adrenal Hyperplasia", Best Pract Res Clin Endocrinol Metab., 2009, 23(2): 181-192.
Mueller et al., "Standard enrichment methods for targeted next-generation sequencing in high-repeat genomic regions", Genetics in Medicine, 2013, 15(11): 910-911.
Product literature for NEXTflex® Congenital Adrenal Hyperplasia Amplicon Panel (For Illumina® Platforms), Catalog #NOVA-4244-01, Bioo Scientific Corporation, 2017, 28 pages.

* cited by examiner

RP1, C4A, CYP21A1P, TNXA – RP2, C4B, CYP21A2, TNXB (functional)
30 kb

B

TNXB    ACCACCTCCCTTTCACCCTCCTCGTTCTCTCTCAACTCCCACCCATGCCGTTTTCTTGGC
        ||||||||||||||||||||||||||||||||||||||||||||||||||||||||||| |
TNXA    ACCACCTCCCTTTCACCCTCCTCGTTCTCTCTCAACTCCCACCCATGCCGTTTTCTTGAC

TCCCACCT CTTGCCCGGGTCCCAGTCCATCTCACCCGTGGTGAGGAAGCCTGTGAGAGC
        ||||||||
        TCCCACCT

CTCACTCTCCTCAAAGCCTCGGACCGAGACCACGGTCACCTCATAGCCAGCCGCCTGGGAT

CAGCCCCCTGGAGTTTCTGGGTCCGGGCCTGGCCATCCACCTGCACACTCTGAGGCTCCC
                 |||||||||||||||||||| |||| ||||||||||||||||||||||||||
                 GGAGTTTCTGGGTCCGGGCCCGGCCGTCCACCTGCACACTCTGAGGCTCCC

GENETIC TEST FOR DETECTING CONGENITAL ADRENAL HYPERPLASIA

BACKGROUND

Congenital adrenal hyperplasia (CAH) is any of several autosomal recessive diseases resulting from mutations of genes for enzymes mediating the biochemical steps of production of mineralocorticoids, glucocorticoids or sex steroids from cholesterol by the adrenal glands (steroidogenesis). Most of these conditions involve excessive or deficient production of sex steroids and can alter development of primary or secondary sex characteristics in some affected infants, children, or adults. The frequency of non-classic (moderate) forms of CAH in the general population is 1:500 to 1:100, and the frequency of the classic (severe) form of CAH in the general population is about 1:10,000.

Each form of CAH is associated with a specific defective gene. The most common type (95% of cases) involves the CYP21A2 gene, which encodes the 21-hydroxylase. The CYP21A2 gene is found on 6p21.3 and is part of the RCCX locus, which is within the human MHC class III region of chromosome 6. The RCCX locus contains one or more copies of a module of four genes that are arranged in tandem: RP, complement C4, steroid 21-hydroxylase (CYP21), and tenascin X (TNX). In about 5% of the population, the RCCX locus contains only one copy of the module. In about 80% of the population, the RCCX locus is bimodular in that it contains two copies of the module. In these cases the RCCX locus contains another C4 locus, CYP21A1P (which is a pseudogene of CYP21A2), and partially duplicated gene segments TNXA and RP2. In about 10-15% of the population, the RCCX locus contains multiple copies of the module. In these cases, the sequence of genes may be RP1, C4A, CYP21A1P, TNXA-RP2 CYP21A2, C4B, TNXB-RP2, CYP21A2, C4B, TNXB.

Three types of genomic alteration in the CYP21A2 gene cause CAH: single nucleotide mutations, chimeras between CYP21A2 and the CYP21A1P pseudogene (which lies upstream of CYP21A2 in genomes that contain a bimodular RCCX locus) and gene duplications (which are frequently asymptomatic because they often still contain a wild type CYP21A2 gene). CAH is associated with single nucleotide mutations in CYP21A2 in about 70% of cases. These mutations may be generated by de novo or by gene conversion with the CYP21A1P pseudogene. In approximately 30% of cases, CAH is associated with a 30 kb deletion caused by recombination between CYP21A2 and the CYP21A1P pseudogene. There are currently nine different deletions described in the literature and these always cause a severe phenotype because the CYP21A2/CYP21A1P chimeras always contain the CYP21A1P pseudogene promoter and, as such, are not expressed. The remainder of the cases (caused by duplication of CYP21A2) are rare because an additional wild type allele can compensate for two mutated alleles and patients with at least one wild type allele of CYP21A2 are asymptomatic.

Traditional approaches for sequencing CYP21A2 involve amplifying the CYP21A2 gene by PCR and then sequencing the PCR products. However, such approaches have been severely confounded by the sequence of the CYP21A1P pseudogene, which is inactive but has a sequence that is about 99% identical to the sequence of the CYP21A2 gene and also contains sequence variations that would be deleterious if they are transferred to the CYP21A2 gene (see, e.g., Tsai et al Anal Biochem. 2011 15: 133-141 and Concolino et al Clin Chem Lab Med. 2010 15: 1057-1062). As such, most if not all of the current approaches for analyzing the sequence of the CYP21A2 gene do so using primers that are designed to only amplify the CYP21A2 gene and not the pseudogene (see, e.g., Cradic et al BMC Med Genet. 2014; 15: 19 and Mueller et al Genetics in Medicine 2013 15 910-911). These approaches, however, are not always effective and do not amplify chimeras between CYP21A2 and the nearby pseudogene.

Thus, a need exists for a better way to analyze the CYP21A2 gene at the molecular level.

SUMMARY

This disclosure provides, among other things, a method for amplifying a CYP21A2 gene and/or a CYP21A2 gene chimera from a sample comprising human genomic DNA. In some embodiments, the method may comprise amplifying a product from a sample comprising human genomic DNA by PCR using a forward primer that is complementary to a sequence that is duplicated in the bimodular human RCCX locus and a reverse primer that is complementary to a sequence that occurs only once in the bimodular human RCCX locus at a position that is downstream of the CYP21A2 gene.

A workflow for analyzing the amplification product to identify mutations in the CYP21A2 gene is also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Before describing exemplary embodiments in greater detail, the following definitions are set forth to illustrate and define the meaning and scope of the terms used in the description.

Numeric ranges are inclusive of the numbers defining the range. Unless otherwise indicated, nucleic acids are written left to right in 5' to 3' orientation; amino acid sequences are written left to right in amino to carboxy orientation, respectively.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "nucleic acid sample," as used herein denotes a sample containing nucleic acid.

The term "oligonucleotide" as used herein denotes a single stranded multimer of nucleotides of about 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

The term "duplex," or "duplexed," as used herein, describes two complementary polynucleotides that are base-paired, i.e., hybridized together.

The term "primer" as used herein refers to an oligonucleotide that has a nucleotide sequence that is complementary to a region of a target polynucleotide. A primer binds to the complementary region and is extended, using the target nucleic acid as the template, under primer extension conditions. A primer may be in the range of about 15 to about 50 nucleotides although primers outside of this length may be used. A primer can be extended from its 3' end by the action of a polymerase. An oligonucleotide that cannot be extended from it 3' end by the action of a polymerase is not a primer. A primer that is "complementary" to a sequence is a primer has a 3' end that contains at least 8 bases (e.g., at least 10, at least 12 or at least 15 bases) of perfect complementarity to the sequence and that is capable of priming nucleic acid synthesis from that sequence.

The term "extending" as used herein refers to any addition of one or more nucleotides to the end of a nucleic acid, e.g. by using a polymerase.

The term "amplifying" as used herein refers to generating one or more copies of a target nucleic acid, using the target nucleic acid as a template.

The terms "determining", "measuring", "evaluating", "assessing," "assaying," "detecting," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end.

As used herein, the term "reaction mixture" refers to a mixture of reagents that are capable of reacting together to produce a product in appropriate external conditions over a period of time. A reaction mixture may contain PCR reagents, for example, the recipes for which are independently known in the art.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., Mg2+) may also be present. PCR reagents may optionally contain a template from which a target sequence can be amplified.

"Genetic locus," "locus,", "locus of interest", "region" or "segment" in reference to a genome or target polynucleotide, means a contiguous sub-region or segment of the genome or target polynucleotide. As used herein, genetic locus, locus, or locus of interest may refer to the position of a nucleotide, a gene, multiple genes or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it.

The terms "plurality", "population" and "collection" are used interchangeably to refer to something that contains at least 2 members. In certain cases, a plurality, population or collection may have at least 10, at least 100, at least 1,000, at least 10,000, at least 100,000, at least $10^6$, at least $10^7$, at least $10^8$ or at least $10^9$ or more members.

The term "adaptor" refers a sequence that is added (e.g., by ligation) to a nucleic acid. An adaptor may be from 5 to 100 bases in length, and may provide, e.g., an amplification primer binding site, a sequencing primer binding site, and/or a molecular identifier such as a sample identifier sequence or molecule identifier sequence. An adaptor may be added to the 5' end, the 3' end, or both ends of nucleic acid molecule. A double stranded adaptor can be added to a fragment by ligating only one strand of the adaptor to the fragment.

The terms "sample identifier sequence", "sample index" and "index" refer to a sequence of nucleotides that is appended to a target polynucleotide, where the sequence identifies the source of the target polynucleotide (i.e., the sample from which sample the target polynucleotide is derived). In use, each sample is tagged with a different sample identifier sequence (e.g., one sequence is appended to each sample, where the different samples are appended to different sequences), and the tagged samples are pooled. After the pooled sample is sequenced, the sample identifier sequence can be used to identify the source of the sequences. A sample identifier sequence may be added to the 5' end of a polynucleotide or the 3' end of a polynucleotide. In certain cases some of the sample identifier sequence may be at the 5' end of a polynucleotide and the remainder of the sample identifier sequence may be at the 3' end of the polynucleotide.

The term "next generation sequencing" refers to the so-called highly parallelized methods of performing nucleic acid sequencing and comprises the sequencing-by-synthesis or sequencing-by-ligation platforms currently employed by Illumina, Life Technologies, Pacific Biosciences and Roche, etc. Next generation sequencing methods may also include, but not be limited to, nanopore sequencing methods such as offered by Oxford Nanopore or electronic detection-based methods such as the Ion Torrent technology commercialized by Life Technologies.

The term "sequence read" refers to the output of a sequencer. A sequence read typically contains a string of Gs, As, Ts and Cs, of 50-1000 or more bases in length and, in many cases, each base of a sequence read may be associated with a score indicating the quality of the base call.

The terms "assessing the presence of" and "evaluating the presence of" include any form of measurement, including determining if an element is present and estimating the amount of the element. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent.

Other definitions of terms may appear throughout the specification.

DETAILED DESCRIPTION

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Figure 1:
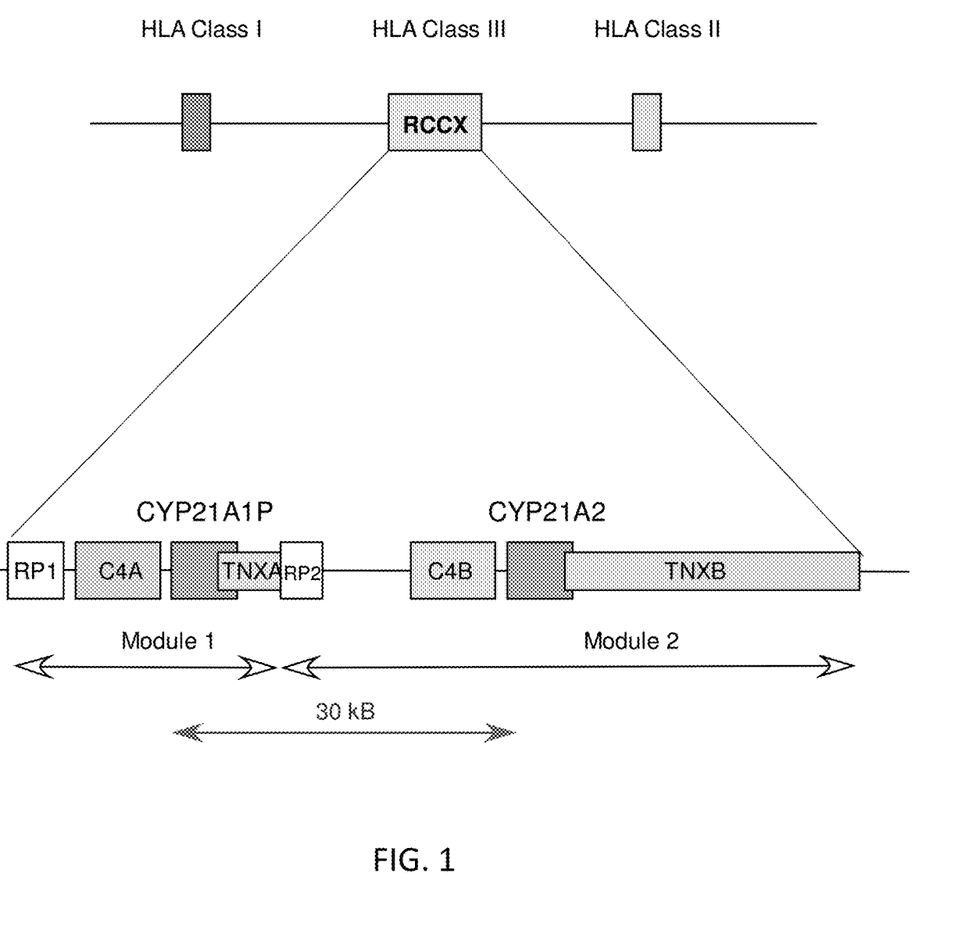
FIG. 1 shows the structure of a bimodular RCCX locus in the HLA class III region of the human genome.
Figure 2:
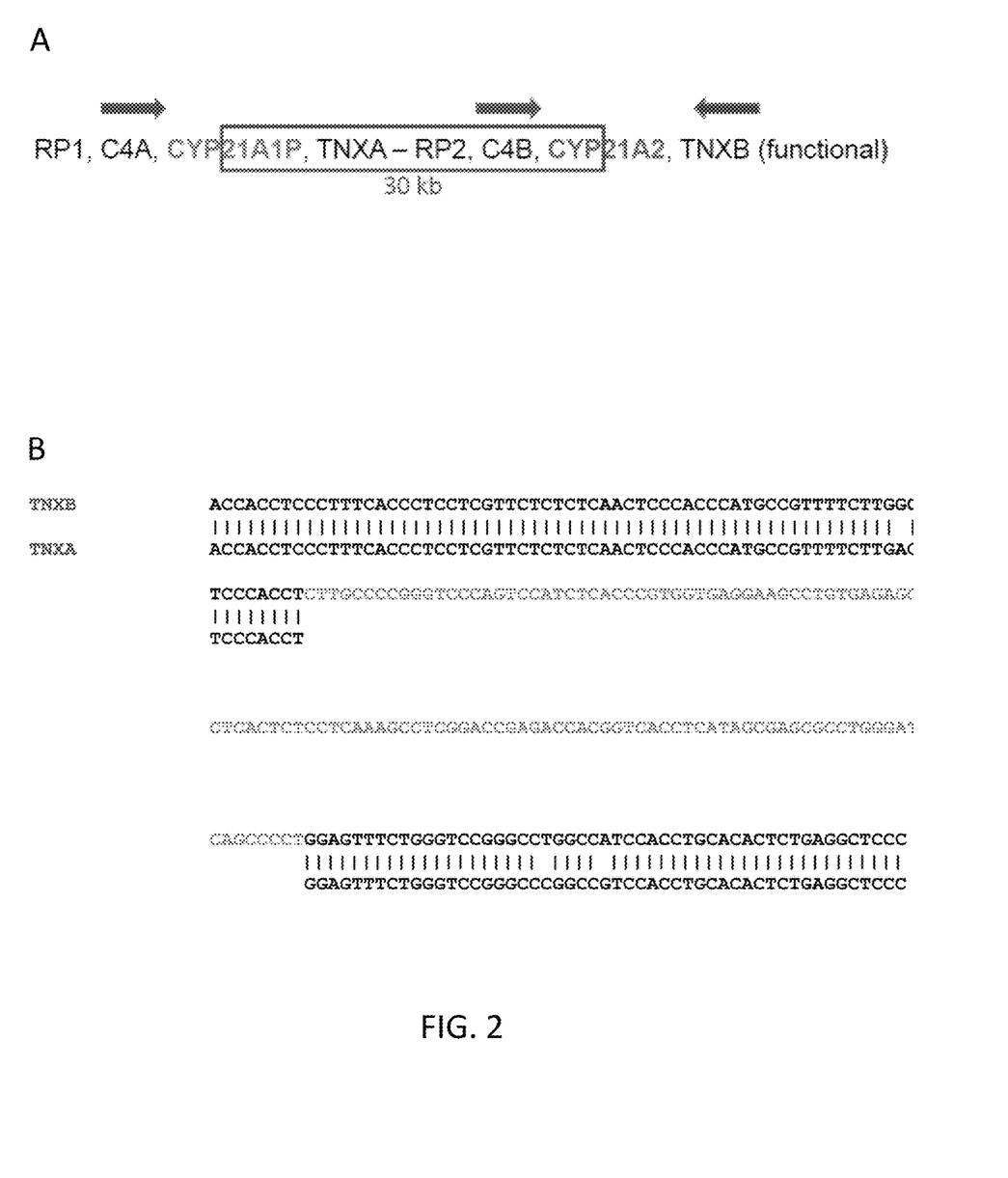
FIG. 2 shows the design of the primers used in the initial PCR step of the method (A) and the sequence of the TNXB and TNXA genes (SEQ ID NOS: 1 and 2, respectively).
Figure 3:
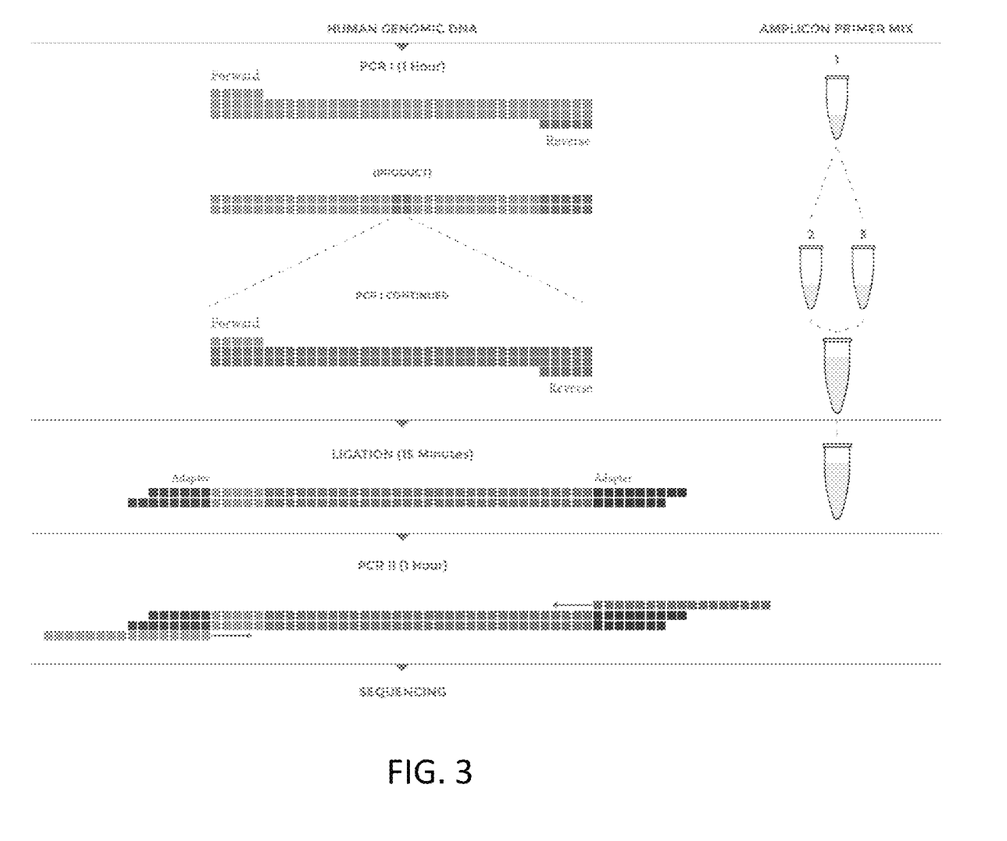
FIG. 3 is a flow-chart summarizing some of the sample processing steps of one implementation of the present method.
Figure 4:
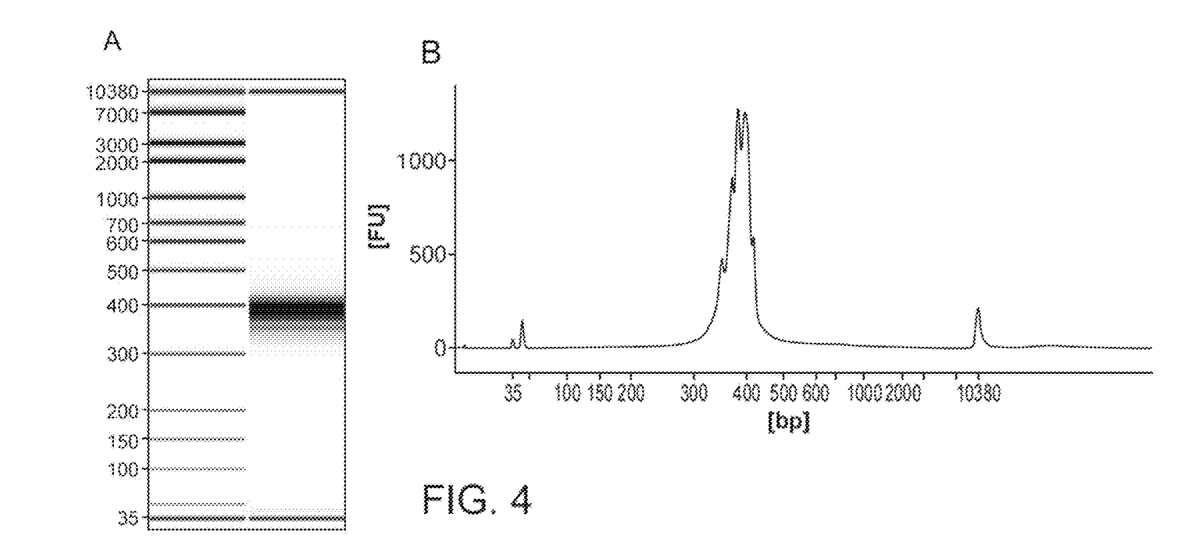
FIG. 4 shows exemplary results. Panel A shows a Bioanalyzer gel image of the amplicons produced by processing a sample of 20 ng of human genomic DNA following the protocol set forth in the examples section of this disclosure. Panel B is an electropherogram of the same.
Figure 5:
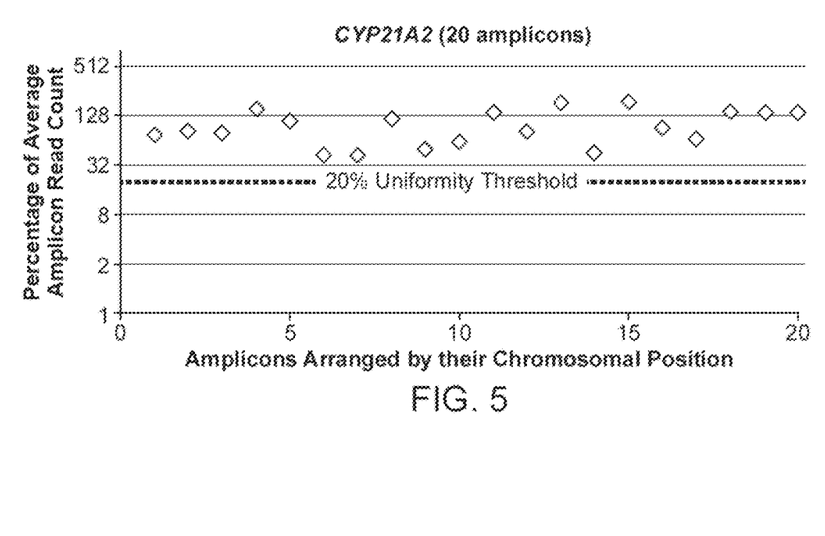
FIG. 5 is a chart showing the performance of 20 amplicons produced using the method set forth in the examples section of this disclosure and sequenced using an Illumina sequencing platform. This example shows the amplicons arranged by their chromosomal position.

This disclosure provides, among other things a method for amplifying a CYP21A2 gene and/or a CYP21A2 gene chimera from a sample comprising human genomic DNA. In some embodiments, the method may comprise amplifying a product from a sample comprising human genomic DNA by PCR using: i. a forward primer that is complementary to a sequence that is duplicated in a bimodular human RCCX locus, where the first occurrence of the duplicated sequence is upstream of the CYP21A1P gene and the second occurrence of the duplicated sequence is between the CYP21A2 gene and the CYP21A1P pseudogene and ii. a reverse primer that is complementary to a sequence that occurs only once in the bimodular human RCCX locus at a position that is downstream of the CYP21A2 gene. The bimodular human RCCX locus is schematically illustrated in FIG. 1. As shown, each module of a bimodular human RCCX locus contains the following genes, in order: RP, C4, CYP21 and TNX genes. The module that contains the CYP21A1P pseudogene upstream of the module that contains the CYP21A2 gene, and the distance between the beginning of the CYP21A1P pseudogene is and the beginning of the coding sequence of the CYP21A2 gene is about 30 kb. Exemplary primer binding sites for forward and reverse primers that can be used in the present method are mapped onto the bimodular human RCCX locus in FIG. 2, panel A. In this example, the forward primer binds to a sequence that is in both the C4A and C4B sequences, whereas the reverse primer binds to sequence that is unique to the TNXB gene (i.e., not in the TNXA gene). In this example, the exact positioning of the forward primer binding site within the C4A/C4B sequences is not critical and, because the C4A and C4B sequences are almost identical, there are many sequences that are duplicated in those genes that the forward primer could bind to. As shown in FIG. 2, panel B, TNXA contains a deletion relative to TNXA. As such, the reverse primer can be designed to hybridize to that sequence, i.e., the sequence that is only in TNXB but not TNXA. Again, the exact positioning of the reverse primer binding site within the TNXB sequence is not critical. This PCR amplification step can be done using long-range PCR (see, e.g., Jia et al, Scientific Reports 2014 4: 5737).

Because the forward primer binds to a sequence that is upstream of the CYP21A1P pseudogene and also between the pseudogene and the CYP21A2 gene, two products could be made, in theory. As would be apparent from a review of FIG. 2A, the first product would be amplified from the forward primer binding site in C4A and the reverse primer binding site in TNXB and would be about 40 kb in length. The second product would be amplified from the forward primer binding site in C4B and the reverse primer binding site in TNXB and would be about 10 kb to 12 kb in length, depending on the primers used. In practice, however, the longer fragment not is amplified and, as such, if the human genomic DNA in the sample contains a bimodular human RCCX (the structure of which is shown in FIG. 1) then only the shorter of the two theoretical amplification product, i.e., the product of 10 kb to 12 kb in length that contains the CYP21A2 gene but not the CYP21A1P pseudogene, is produced. However, if the locus has been rearranged (i.e., by recombination between the CYP21A1P pseudogene and the CYP21A2 gene) the product of the reaction will contain the sequence of the CYP21A1P/CYP21A2 chimera (amplified from the forward primer binding site in C4A and the reverse primer binding site in TNXB). In the latter case, approximately 30 kb of sequence will have been removed from the locus and the resulting product (which will again be of 10 kb to 12 kb in length) will contain the sequence of the CYP21A1P/CYP21A2 chimera. Thus, if the RCCX locus is not rearranged then the product will contain the sequence of the CYP21A2 gene but not the CYP21A1P pseudogene and, if the RCCX locus has been rearranged and contains a chimera between the CYP21A2 gene and the CYP21A1P pseudogene, then the product will contain the sequence of the CYP21A1P/CYP21A2 chimera. In other words: (i) the product of the reaction contains the sequence of the CYP21A2 gene but not the sequence of the CYP21A1P pseudogene if the human genomic DNA comprises a CYP21A2 gene that has not been rearranged; and (ii) the product contains the sequence of the CYP21A1P/CYP21A2 gene chimera if the human genomic DNA comprises an RCCX locus that has been rearranged to produce a CYP21A1P/CYP21A2 gene chimera.

In some embodiments, the method may further comprise amplifying a plurality of segments (e.g., 10-30 segments) of the product of the initial amplification step by PCR using multiple primer pairs, wherein the primer pairs hybridize to sequences that are in both the CYP21A2 gene and the CYP21A1P pseudogene. This primers do not distinguish between the CYP21A2 gene and the CYP21A1P pseudogene and this step of the method should amplify multiple products (a product for each primer pair) regardless of whether the sample contains a CYP21A2 gene, a CYP21A1P/CYP21A2 gene chimera or both. This amplification step (referred to as PCR I in the example) may be done by PCR using a limited number of cycles (e.g., 10-20 cycles). If the products of this reaction are going to be sequenced then the length of the segments that are amplified may be tailored to the sequencing platform used for sequencing. For example, in some embodiments, the length of the segments may in the range of 100 bp to 1 kb, e.g., 150 bp to 500 bp. The segments amplified in this step of the method may comprise the sequence of all 10 exons of the CYP21A2 gene.

In some embodiments, at least some of the segments amplified in this step of the method may be overlapping, i.e., may have a sequence at an end that overlaps with a sequence in another segment. In these embodiments, the amplifying may be done in i. a first multiplex PCR reaction that comprises some but not all of the primer pairs (e.g., 2-20 or 5-15) primer pairs; and ii. a second multiplex PCR reaction that comprises some or all of the remainder of the primer pairs (e.g., 2-20 or 5-15 primer pairs). In these embodiments, the segments amplified by the first multiplex PCR reaction are not overlapping, the segments amplified by the second multiplex PCR reaction are not overlapping, and at least some of the segments amplified by the first multiplex PCR reaction overlap with the segments amplified by the second PCR reaction. As would be apparent, this part of the method may comprise pooling the products amplified in the first multiplex PCR reaction with the products of the second multiplex PCR reaction, prior to analysis.

After amplifying the segments, the method may comprise ligating an adapter onto the products to produce adapter-ligated amplicons. The adaptors provide binding sites for PCR primers that are used in the next step of the method and, as such, they usually are at least 12 bp long (e.g., at least 15 bp or at least 20 bp long). In certain cases, a Y adaptor, e.g., adaptor that contains: a double-stranded region and a single-stranded region in which the oligonucleotides are not complementary, may be used. In these cases, the end of the double-stranded region ligates to the fragments, and each strand of the product is asymmetrically tagged in that it has the sequence of one strand of the Y-adaptor at one end and the other strand of the Y-adaptor at the other end. In other embodiments, a loop adaptor (as described in U.S. Pat. No. 8,420,319) may be used.

In the next step of the method, the adapter-ligated amplicons may be amplified using primers that hybridize to a sequence in the adapter, or a complement thereof, to produce a second amplification product. Again, this step may be done by PCR using a limited number of cycles. In some embodiments, the primers used in this step of the method indexed, thereby allowing difference samples to be pooled together prior to analysis.

As would be apparent, the adaptors ligated to the amplicons and/or the primers used for amplification may be compatible with use in a next generation sequencing platform, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al. (Nature 2005 437: 376-80); Ronaghi et al. (Analytical Biochemistry 1996 242: 84-9); Shendure (Science 2005 309: 1728); Imelfort et al. (Brief Bioinform. 2009 10:609-18); Fox et al. (Methods Mol Biol. 2009; 553:79-108); Appleby et al. (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps.

Next, the method comprises sequencing the second amplification product to produce a plurality of sequence reads. This step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads.

The sequence reads can be examined to determine if the human genomic DNA comprises a mutation in the CYP21A2 gene. After trimming/filtering/grouping the reads, this step of method may comprise comparing the sequence reads to a reference sequence (which could be sequence of the CYP21A1P pseudogene or the CYP21A2 gene) and determining whether the human genomic DNA in the sample comprises a CYP21A2 gene that has a de novo mutation, a CYP21A2 gene that comprises pseudogene-like mutation introduced by gene conversion between the CYP21A2 gene and the CYP21A1P pseudogene, or CYP21A2/CYP21A1P chimera generated by a rearrangement in the RCCX locus.

The sample of human genomic DNA may be obtained from any suitable tissue. For example, the DNA may be isolated from a soft tissue or from a bodily fluid, or from a cell culture that is grown in vitro. In some embodiments the sample of human genomic DNA may be conveniently made from nucleated cells in the peripheral blood (see, e.g., Ghatak et al J Biomol Tech. 2013 24: 224-231).

EMBODIMENTS

Embodiment 1

A method for amplifying a CYP21A2 gene and/or a CYP21A2 gene chimera from a sample, comprising: amplifying a product from a sample comprising human genomic DNA by PCR using:
  i. a forward primer that is complementary to a sequence that is duplicated in a bimodular human RCCX locus, wherein the bimodular human RCCX locus comprises a CYP21A2 gene and a CYP21A1P pseudogene that is approximately 30 kb upstream of the CYP21A2 gene, and:
    the first occurrence of the duplicated sequence is upstream of the CYP21A1P pseudogene; and
    the second occurrence of the duplicated sequence is between the CYP21A2 gene and the CYP21A1P pseudogene; and
  ii. a reverse primer that is complementary to a sequence that occurs only once in the bimodular human RCCX locus at a position that is downstream of the CYP21A2 gene, wherein:
    the product contains the sequence of the CYP21A2 gene but not the sequence of the CYP21A1P pseudogene if the human genomic DNA comprises a CYP21A2 gene that has not been rearranged; and,
    the product contains the sequence of the CYP21A1P/CYP21A2 gene chimera if the human genomic DNA comprises an RCCX locus that has been rearranged to produce a CYP21A1P/CYP21A2 gene chimera.

Embodiment 2

The method of embodiment 1, further comprising: amplifying a plurality of segments of the product by PCR using multiple primer pairs, wherein the primer pairs hybridize to sequences that are in both the CYP21A2 gene and the CYP21A1P pseudogene.

Embodiment 3

The method of embodiment 2, wherein the median length of the segments is in the range of 100 bp to 1 kb.

Embodiment 4

The method of any of embodiments 2-3, wherein the median length of the segments is in the range of 150 bp to 500 bp.

Embodiment 5

The method of any of embodiments 2-4, wherein the segments comprise all 10 exons of the CYP21A2 gene.

Embodiment 6

The method of any of embodiments 2-5, wherein at least some of the amplified segments are overlapping.

Embodiment 7

The method of embodiment 6, wherein the amplifying is done in: i. a first multiplex PCR reaction that comprises some but not all of the primer pairs; and ii. a second multiplex PCR reaction that comprises the remainder of the primer pairs;
  wherein:
    the segments amplified by the first multiplex PCR reaction are not overlapping;
    the segments amplified by the second multiplex PCR reaction are not overlapping; and
    at least some of the segments amplified by the first multiplex PCR reaction overlap with the segments amplified by the second PCR reaction.

Embodiment 8

The method of embodiment 7, further comprising pooling the products amplified in the first multiplex PCR reaction with the products of the second multiplex PCR reaction.

Embodiment 9

The method of any of embodiments 2-8, further comprising:
  ligating an adapter onto the amplified segments to produce adapter-ligated amplicons.

Embodiment 10

The method of embodiment 9, further comprising
  amplifying the adapter-ligated amplicons using primers that hybridize to a sequence in the adapter or a complement thereof to produce a second amplification product.

Embodiment 11

The method of embodiment 10, wherein the primers are indexed.

Embodiment 12

The method of embodiments 10-11, further comprising:
  sequencing the second amplification product to produce a plurality of sequence reads.

Embodiment 13

The method of embodiment 12, further comprising
  analyzing the sequence reads to determine if the human genomic DNA comprises a mutation in the CYP21A2 gene.

Embodiment 14

The method of embodiment 13, wherein the mutation is a de novo mutation, pseudogene-like mutation introduced by gene conversion between the CYP21A2 gene and the CYP21A1P pseudogene or a rearrangement in the RCCX locus that produces a CYP21A2/CYP21A1P chimera.

EXAMPLES

The following protocol describes a molecular diagnostic for CAH. This example involves: (a) enrichment of DNA by long-range PCR of locus CYP21A2 and/or of CYP21A1P/CYP21A2 chimeras if present, in one tube; (b) Enrichment of this locus by short-range PCR targeting CYP21A2 in two separate tubes; and (c) Final library construction by adapter ligation and amplifications with barcoded primers.

Step A: PCR I—Targeted Congenital Adrenal Hyperplasia Amplification

1. For each sample, prepare one separate reaction per sample using CAH Amplicon Primer Mix 1 by combining the following reagents in adjacent wells in a PCR plate. Note: It is recommended to combine these reagents as a master mix if processing multiple samples.

Reaction 1:

| | |
|---|---|
| — μL | Genomic DNA (20-100 ng in up to 15.6 μL) |
| — μL | Nuclease-free Water |
| 2 μL | NEXTflex® CAH Amplicon Primer Mix 1 |
| 0.5 μL | NEXTflex® PCR Enhancer 1 |
| 0.9 μL | NEXTflex® PCR Enhancer 4 |
| 6 μL | NEXTflex® Hot Start PCR I Master Mix |
| 25 μL | TOTAL |

2. Mix thoroughly by pipette.
3. Apply adhesive PCR plate seal and place in thermocycler for the following PCR cycles:

| |
|---|
| 2 min 98° C. |
| 15 cycles of |
| 20 sec 98° C. |
| 30 sec 69° C. |
| 6 min 72° C. |
| then |
| 5 min 72° C. |
| Hold 4° C. |

4. For each sample, prepare two separate reactions using CAH Primer Mix 2 and 3 by combining the following reagents in adjacent wells in a PCR plate.

Reaction 2:

| | |
|---|---|
| 3 μL | Reaction 1 |
| 15.7 μL | Nuclease-free Water |
| 2.4 μL | NEXTflex® CAH Amplicon Primer Mix 2 |
| 0.6 μL | NEXTflex® PCR Enhancer 1 |
| 1.1 μL | NEXTflex® PCR Enhancer 4 |
| 7.2 μL | NEXTflex® Hot Start PCR I Master Mix |
| 30 μL | TOTAL |

Reaction 3:

| | |
|---|---|
| 3 μL | Reaction 1 |
| 15.7 μL | Nuclease-free Water |
| 2.4 μL | NEXTflex® CAH Amplicon Primer Mix 3 |
| 0.6 μL | NEXTflex® PCR Enhancer 1 |
| 1.1 μL | NEXTflex® PCR Enhancer 4 |
| 7.2 μL | NEXTflex® Hot Start PCR I Master Mix |
| 30 μL | TOTAL |

5. Mix thoroughly by pipette.
6. Apply adhesive PCR plate seal and place in thermocycler for the following PCR cycles:

| |
|---|
| 2 min 98° C. |
| two cycles of: |
| 20 sec 98° C. |
| 4 min 70° C. |
| then four cycles of: |
| 20 sec 98° C. |
| 4 min 68° C. |
| then five cycles of: |
| 20 sec 98° C. |
| 4 min 66° C. |
| then five cycles of: |
| 20 sec 98° C. |
| 4 min 64° C. |
| then |
| Hold 4° C. |

7. Proceed immediately to Step B: PCR I Cleanup.

Step B: PCR I Cleanup

1. Add 1 μL NEXTflex® Stop Solution to each reaction, mix thoroughly, and incubate for 30 seconds. Combine reactions 2 and 3 from previous step.

2. Add 37 μL of NEXTflex® Cleanup Beads to each sample. Mix thoroughly until homogenized.

3. Incubate at room temperature for 5 minutes.

4. Place the 96 well PCR Plate on the magnetic stand at room temperature for 5 minutes, or until the supernatant appears completely clear.

5. Do not discard the supernatant in this step. Transfer the clear supernatant to a new well. Be careful not to disrupt the magnetic bead pellet or transfer any magnetic beads with the supernatant.

6. Add 37 μL of NEXTflex® Cleanup Beads to supernatant. Mix thoroughly until homogenized.

7. Incubate at room temperature for 5 minutes.

8. Place the 96 well PCR plate on the magnetic stand at room temperature for 5 minutes, or until the supernatant appears completely clear.

9. Remove and discard the supernatant. Do not disturb beads. Some liquid may remain in wells.

10. With plate on stand, gently add 200 μL of freshly prepared 80% ethanol to each magnetic bead pellet and incubate plate at room temperature for 30 seconds. Carefully remove ethanol by pipette.

11. Repeat previous step, for a total of 2 ethanol washes. Ensure all ethanol has been removed.

12. Remove the plate from the magnetic stand and let dry at room temperature for 5 minutes, or until bead pellet is visibly dry.

13. Resuspend dried beads with 30 μL of Resuspension Buffer. Mix thoroughly by pipetting.

Ensure beads are no longer attached to the side of the well.

14. Incubate resuspended beads at room temperature for 3 minutes.

15. Place the 96 well PCR plate on the magnetic stand at room temperature for 5 minutes, or until sample appears clear.

16. Transfer 28 μL of clear supernatant (purified PCR I Reaction) to new well.

17. Proceed immediately to Step C: Adapter Ligation.

Step C: Adapter Ligation

1. For each sample, combine the following reagents on ice in a nuclease-free 96 well PCR Plate:

| | |
|---|---|
| 28 μL | Purified PCR I Reaction |
| 2.5 μL | NEXTflex ® Amplicon DNA Adapter |
| 42 μL | NEXTflex ® Ligation Mix |
| 72.5 μL | TOTAL |

2. Mix thoroughly by pipette.
3. Apply adhesive PCR plate seal and incubate in a thermocycler for 15 minutes at 22° C.
4. Proceed immediately to Step D: Cleanup.

Step D: Cleanup

1. Add 58 μL of NEXTflex® Cleanup Beads to each sample. Mix thoroughly until homogenized.
2. Incubate at room temperature for 5 minutes.
3. Place the 96 well PCR Plate on the magnetic stand at room temperature for 5 minutes, or until the supernatant appears completely clear.
4. Remove and discard the supernatant. Do not disturb beads. Some liquid may remain in wells.
5. With plate on stand, gently add 200 μL of freshly prepared 80% ethanol to each magnetic bead pellet and incubate plate at room temperature for 30 seconds. Carefully remove ethanol by pipette.
6. Repeat previous step, for a total of 2 ethanol washes. Ensure all ethanol has been removed.
7. Remove the plate from the magnetic stand and let dry at room temperature for 5 minutes or until bead pellet is visibly dry.
8. Resuspend dried beads with 40 μL of Resuspension Buffer. Mix thoroughly by pipetting.
Ensure beads are no longer attached to the side of the well.
9. Incubate resuspended beads at room temperature for 3 minutes.
10. Place the 96 well PCR plate on the magnetic stand at room temperature for 5 minutes, or until sample appears clear.
11. Gently transfer 38 μL of clear sample to new well.
12. Proceed immediately to Step E: PCR II Amplification.

Step E: PCR II Amplification

1. For each sample, combine the following reagents on ice in a nuclease-free 96 well PCR Plate:

| | |
|---|---|
| 38 μL | Purified Adapter Ligated DNA (from Step D) |
| 2 μL | NEXTflex ® PCR II Barcoded Primer Mix |
| 10 μL | NEXTflex ® PCR II Master Mix |
| 50 μL | TOTAL |

2. Mix thoroughly by pipette.
3. Apply adhesive PCR plate seal and place in thermocycler for the following PCR cycles:

```
20 min 65° C.
2 min 98° C.
12 cycles of:
  30 sec 98° C.
  30 sec 65° C.
  60 sec 72° C.
then
4 min 72° C.
Hold 4° C.
```

4. Remove PCR plate from the thermocycler. Add 40 μL of NEXTflex® Cleanup Beads to each sample and mix thoroughly until homogenized.
5. Incubate at room temperature for 5 minutes.
6. Place the 96 well PCR Plate on the magnetic stand at room temperature for 5 minutes, or until the supernatant appears completely clear.
7. Remove and discard the supernatant. Do not disturb beads. Some liquid may remain in wells.
8. With plate on stand, gently add 200 μL of freshly prepared 80% ethanol to each magnetic bead pellet and incubate plate at room temperature for 30 seconds. Carefully remove ethanol by pipette.
9. Repeat previous step, for a total of 2 ethanol washes. Ensure all ethanol has been removed.
10. Remove the plate from the magnetic stand and let dry at room temperature for 5 minutes or until bead pellet is visibly dry.
11. Resuspend dried beads with 22 μL of Resuspension Buffer. Mix thoroughly by pipetting.
Ensure beads are no longer attached to the side of the well.
12. Incubate resuspended beads at room temperature for 3 minutes.
13. Place the 96 well PCR plate on the magnetic stand at room temperature for 5 minutes, or until sample appears clear.
14. Gently transfer 20 μL of clear sample to a new well and proceed to library analysis or seal plate with adhesive PCR plate seal and store at −20° C. Qubit™ fluorometer (Thermo Fisher Scientific®) and LabChip® GXII Touch HT instrument (PerkinElmer®) are recommended to quantify and analyze quality of the library.

After the step E, the products may be sequenced and the sequence reads may be processed using the following steps:
1. Import demultiplexed fastq files from sequencing machine
2. Trim/Filter reads
   a. Trim adapters from 3' end of reads
   b. Subsequently remove reads shorter less than 70 bp
3. Trim the 5' primers sequences from the sorted reads based on primer FASTA files provided (NOVA-4244_Congenital_Adrenal_Hyperplasia_Primers.fa).
Trim reads at 3' end based on expected length of amplicon without primers.
4. Align to reference sequences. Use the following covered target regions coordinates:

| | | |
|---|---|---|
| For hg38 | CYP21A2 | chr6: 32038278-32041262 |
| For hg19 | CYP21A2 | chr6: 32006055-32009039 |

Alternatively align to genome with hard masked CYP21A1P sequence.
5. Call variants.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

What is claimed is:

1. A method for amplifying a CYP21A2 gene and/or a CYP21A2 gene chimera from a sample, comprising:
   a) amplifying a product from a sample comprising human genomic DNA by PCR using:
      i. a forward primer that is complementary to a sequence that is duplicated in a bimodular human RCCX locus, wherein the bimodular human RCCX locus comprises, in order, an RP1 gene, a C4A gene, a CYP21A1P pseudogene, a TNXA gene, an RP2 gene, a C4B gene, a CYP21A2 gene and a TNXB gene, and:
         the first occurrence of the duplicated sequence is in the C4A gene and/or the RP1 gene; and
         the second occurrence of the duplicated sequence is in the C4B gene and/or the RP2 gene; and
      ii. a reverse primer that is complementary to a sequence that occurs only once in the bimodular human RCCX locus at a position in the TNXB gene, wherein:
      the product of (a) contains the sequence of the CYP21A2 gene but not the sequence of the CYP21A1P pseudogene if the human genomic DNA comprises a CYP21A2 gene that has not been rearranged; and,
      the product of (a) contains the sequence of the CYP21A1P/CYP21A2 gene chimera if the human genomic DNA comprises an RCCX locus that has been rearranged to produce a CYP21A1P/CYP21A2 gene chimera; and
   b) amplifying a plurality of segments of the product of (a) by PCR using multiple primer pairs, wherein the primer pairs hybridize to sequences that are in both the CYP21A2 gene and the CYP21A1P pseudogene, wherein at least some of the amplified segments are overlapping, wherein the amplifying is done in:
      i) a first multiplex PCR reaction that comprises some but not all of the primer pairs; and
      ii) a second multiplex PCR reaction that comprises the remainder of the primer pairs;

wherein:
      the segments amplified by the first multiplex PCR reaction are not overlapping;
      the segments amplified by the second multiplex PCR reaction are not overlapping; and
      at least some of the segments amplified by the first multiplex PCR reaction overlap with the segments amplified by the second PCR reaction.

2. The method of claim 1, wherein the median length of the segments is in the range of 100 bp to 1 kb.

3. The method of any of claim 1, wherein the median length of the segments is in the range of 150 bp to 500 bp.

4. The method of any of claim 1, wherein the segments comprise all 10 exons of the CYP21A2 gene.

5. The method of claim 1, further comprising pooling the products amplified in the first multiplex PCR reaction with the products of the second multiplex PCR reaction.

6. The method of any of claim 1, further comprising:
   ligating an adapter onto the amplified segments to produce adapter-ligated amplicons.

7. The method of claim 6, further comprising
   amplifying the adapter-ligated amplicons using primers that hybridize to a sequence in the adapter or a complement thereof to produce a second amplification product.

8. The method of claim 7, wherein the primers are indexed.

9. The method of claim 7, further comprising:
   sequencing the second amplification product to produce a plurality of sequence reads.

10. The method of claim 9, wherein the CYP21A2 gene comprises a mutation and the method further comprises
    identifying the mutation using the plurality of sequence reads.

11. The method of claim 10, wherein the mutation is a de novo mutation, pseudogene-like mutation introduced by gene conversion between the CYP21A2 gene and the CYP21A1P pseudogene or a rearrangement in the RCCX locus that produces a CYP21A2/CYP21A1P chimera.

* * * * *

SEQUENCE LISTING

<160> NUMBER OF SEQ ID NOS: 2

<210> SEQ ID NO 1
<211> LENGTH: 239
<212> TYPE: DNA
<213> ORGANISM: homo sapien

<400> SEQUENCE: 1
accacctccc tttcaccctc ctcgttctct ctcaactccc acccatgccg ttttcttggc      60
tcccacctct tgccccgggt cccagtccat ctcacccgtg gtgaggaagc ctgtgagagg     120
ctcactctcc tcaaagcctc ggaccgagac cacggtcacc tcatagcgag cgcctgggat     180
cagcccctgg agtttctggg tccgggcctg gccatccacc tgcacactct gaggctccc     239

<210> SEQ ID NO 2
<211> LENGTH: 119
<212> TYPE: DNA
<213> ORGANISM: homo sapien

<400> SEQUENCE: 2
accacctccc tttcaccctc ctcgttctct ctcaactccc acccatgccg ttttcttgac      60
tcccacctgg agtttctggg tccgggcccg gccgtccacc tgcacactct gaggctccc     119